United States Patent

Kambara et al.

Patent Number: 5,268,080
Date of Patent: Dec. 7, 1993

[54] DNA DETECTOR AND DNA DETECTION METHOD

[75] Inventors: Hideki Kambara, Hachiouji; Keiichi Nagai, Higashiyamato, both of Japan

[73] Assignee: Hitachi, Ltd., Tokyo, Japan

[21] Appl. No.: 843,232

[22] Filed: Feb. 28, 1992

[30] Foreign Application Priority Data

Feb. 28, 1991 [JP] Japan .................. 3-034006

[51] Int. Cl.⁵ .................. G01N 27/26; G01N 27/447
[52] U.S. Cl. .................. 204/182.8; 204/299 R; 356/344
[58] Field of Search .......... 204/299 R, 182.8; 356/344

[56] References Cited

U.S. PATENT DOCUMENTS 3,764,512 10/1973 Greenwood et al. .......... 204/299 R
4,938,593 7/1990 Morris et al. .......... 356/344
5,062,942 11/1991 Kambara et al. .......... 204/299 R
5,108,179 4/1992 Myers .......... 356/344

Primary Examiner—John Niebling
Assistant Examiner—John S. Starsiak, Jr.
Attorney, Agent, or Firm—Antonelli, Terry, Stout & Kraus

[57] ABSTRACT

In a DNA detecting method wherein the fluorescence detection type electrophoresis apparatus is used, Texas Red is employed as a fluorophor which labels a DNA fragment, the He-Ne laser having an emission wavelength of 594 nm is used as an excitation light, the excitation light irradiates the line portion of the gel plate simultaneously, and a resulting linear fluorescent image is collected by a cylindrical lens and photodetected, thereby providing an apparatus featuring a higher sensitivity, a smaller size and a lighter weight than conventional apparatuses.

8 Claims, 1 Drawing Sheet

DNA DETECTOR AND DNA DETECTION METHOD

BACKGROUND OF THE INVENTION

The present invention relates to a method of detection of DNA and protein and of DNA base sequencing determination and to an apparatus therefor.

For DNA base sequencing determination by electrophoresis gel separation, radioisotope label has been used as a label for a DNA fragment. Due to the inconvenience of this method, however, a method of using a fluorescence label has come to be increasingly employed. (Refer to the U.S. patent application Ser. No. 07/506,986 (U.S. Pat. No. 5,062, 942) and Bio/Technology Vol. 6, July 1988, pp. 816–821, for example.) As an excitation light source this method uses argon laser with an output of 20 to 50 mw and a wavelength of 488 nm or 515 nm to detect the DNA fragment of $10^{16}$ mole/band to $2 \times 10^{-18}$ mole/band As fluorophores, the method has used FITC (fluorescein isothiocyanate with a maximum emission wavelength of 515 nm), SF (succinyl fluorescein with a maximum emission wavelength of 510 nm to 540 nm), TRITC (tetrarhodamine isothiocyanate with a maximum emission wavelength of 580 nm) and Texas Red (sulforhodamine 101 with a maximum emission wavelength of 615 nm).

The above-mentioned conventional technique, however, has disadvantages in that the sensitivity is insufficient, and the entire equipment must be made greater in size because the Ar laser is greater in size than a He-Ne laser.

SUMMARY OF INVENTION

The object of the present invention is to provide a solution to the above-said problems and to provide a method and small-sized device in which extra-sensitive DNA detection is made possible. To achieve the object, the present invention uses a He-Ne laser with an emission wavelength of 594 nm in DNA base sequencing determination by fluorescence detection type electrophoresis gel separation, and adopts a highly efficient photodetecting system.

The measuring limit for the DNA fragment labeled by a fluorophore in the process of electrophoresis gel migration is determined by the intensity and fluctuation of the background fluorescence from the gel with respect to fluorescence for labeling. The background fluorescence from the gel is gradually reduced with the increase of the emission wavelength. Thus, when excited at the optimum wavelength, the quantity of the fluorescence normalized by the background fluorescence from the gel is the greatest in the case of Texas Red. According to this normalized quantity of the fluorescence, the sensitivity of Texas Red is five to ten times that of FITC. In the present invention, there has been used Texas Red or its derivative as a labeling fluorophore, and a He-Ne laser with the wavelength of 594 nm, which is close to the optimum wavelength, as the excitation light source. The wavelength of 594 nm for the excitation light is close to the maximum emission wavelength of the Texas Red which is 615 nm. One of the problems was how to remove the scattered light from the excitation light, and the present invention has succeeded in removing this scattered light by using a sharp-cutting fluorophore filter which will be described below. The output from the He-Ne laser with the wavelength of 594 nm ranges from 1 mW to 7 mW. The output from a typical model of the He-Ne laser (594 nm) is as small as 2 mw, and greater emission strength cannot be obtained; therefore, the detecting sensitivity greatly depends on the fluctuation of the background fluorescence from the gel. To solve this problem, the present invention has improved the photodetecting system, and has adopted a photodetecting system which receives a greater amount of light by two or more digits than the excitation light scanning method. Namely, the excitation light is made to be incident upon the gel plate through the side thereof, and the entire measured area is irradiated simultaneously to increase the overall emission strength. Furthermore, a cylindrical lens is used to increase the photodetecting solid angle.

Changing the wavelength of the excitation light from 488 nm to 594 nm has reduced the background fluorescence from the gel down to approximately one fifth when the laser of the same output is used. In addition, when the conventional argon laser (about 20 mw) is employed, FITC is subjected to photodestruction, and this results in reduced emission strength, and hence reduced sensitivity. By contrast, under the 2.5 mw He-Ne laser irradiation, photodestruction the fluorophore hardly occurs to Texas Red during measurement. This permits the emission strength normalized by the background fluorescence from the gel to be greater by one digit than that of FITC.

In the laser scanning method, the area of 100 mm is swept by the laser beam of approximately 0.3 mm in diameter. Even when the conventional 50 mw laser is used, the average laser intensity with which each point is irradiated is as small as 17 microwatts, since the irradiation time at each point is reduced. When the 2.5 mw laser is used, the average laser intensity is approximately 0.9 microwatts, and this almost cannot be put into practical use. The irradiation intensity is 2.5 mw in the lateral incidence method employed in one of the present embodiments, and this emission is sufficient. However, in the scanning method the photodetecting efficiency can be made approximately 2 percent, but in the simultaneous irradiation method, the fluorescent image is received in a reduced size; therefore the photodetecting efficiency is reduced to 0.1 percent or less.

Defining a solid angle as $\Omega$ and the transmittance of the filter or the like as T, the photodetecting efficiency $\eta$ can be expressed by the following formula (1):

$$\eta = \frac{\Omega T}{4\pi} \quad (1)$$

Assuming the image reduction ratio as m and the f-number of the lens as F, $\omega$ is represented as:

$$\Omega = \frac{\pi}{4(m+1)^2 F^2} \quad (2)$$

Thus, the photodetecting efficiency $\eta$ can be expressed by the following formula (3):

$$\eta = \frac{1}{16(m+1)^2 F^2} \quad (3)$$

where m represents (length of the measured portion)/(length of the detector). In the scanning method, $m < 1$; and in the lateral incident method, $120 \text{ cm}/24 \text{ cm} < m < 120 \text{ cm}/18 \text{ cm}$ by way of an example, namely m is approximately from 5 to 7. Accordingly, the photodetecting rate of the lateral incident method is approximately 1/50, because of the term of $(m+1)^2$ in formula (3), on the one hand. On the other hand, in the case of the scanning method where light is not continuously received from each measured point, the result is multiplied by 3/1000 to 5/1000 as a factor due to duty cycle. Thus, in total, the lateral incident method yields a greater photodetecting efficiency than the scanning method. When the laser having a smaller output such as a He-Ne laser is used, it is important to find a means to obtain a the sufficient photodetecting efficiency. The present invention uses the cylindrical lens to increase the photodetecting efficiency by, for example, four to five times. This system provides a high photodetecting efficiency, ensuring highly sensitive detection of the fluorescent image.

The U.S. patent application Ser. No. 07./506,986 discloses the case of using Texas Red and the He-Ne laser having a wavelength of 543 nm. Compared with the case of using the 594 nm He-Ne laser, the excitation efficiency is as low as ⅓, and the output is also as low as 1 mw.

DESCRIPTION OF THE PREFERRED EMBODIMENTS

Figure 1:
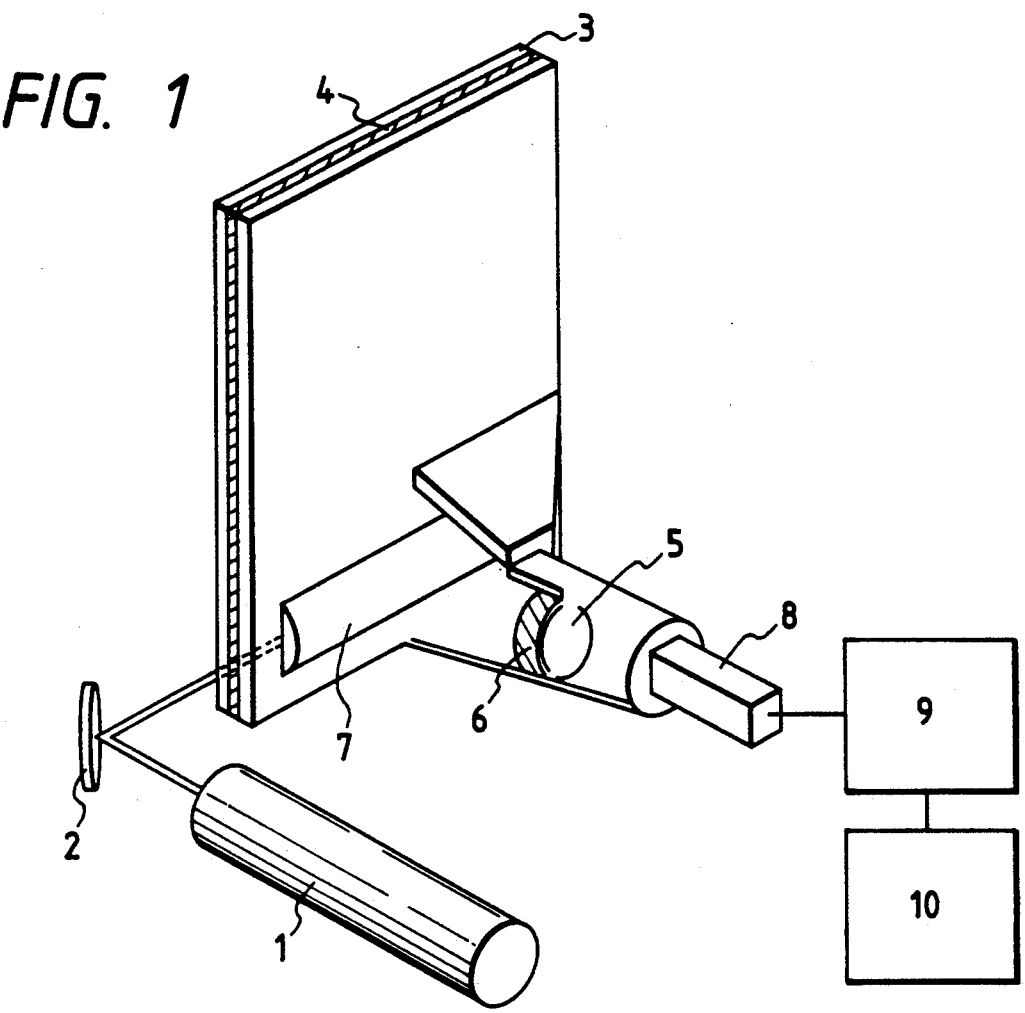
FIG. 1 is a schematic view representing the DNA detector as one of the embodiments of the present invention.

One embodiment of the present invention will be described with reference to FIGS. 1 and 2. FIG. 1 is a schematic view representing the detector. Light emitted from the 594 nm He-Ne laser 1 irradiates the electrophoresis separation gel plate 4 from the side. After being collected by the cylindrical lens 7, the fluorescence emitted from the linearly irradiated portion is filtered out by the band pass filter 6, and forms images on the line sensor or secondary detector 8 through the lens for image formation 5. Filter 6 is a 6-cavity multilayer interference filter with a diameter of 50 mm, and transmittances for light having wavelengths of 594 nm, 600 nm, 610-630 nm and 640 nm are $10^{-4}$, $10^{-2}$, 0.6 or more, and 0.01 or less, respectively.

The concentration of the acrylamide gel constituting the gel plate 4 (concentration of the total quantity of monomer) is 4 to 6 percent (g/cc). When irradiated by the He-Ne laser with the wavelength of 594 nm, the background fluorescence from the gel has the same intensity as the fluorescence from Texas Red having a concentration of $2 \times 10^{-11}$ mole. The laser power is 2.5 mw and the beam diameter is 0.3 mm. The positional resolution on the linearly irradiated portion of 0.5 mm is sufficient. In FIG. 1, the reference numeral 2 denotes a reflection mirror, 3 a glass plate holding the gel plate 4, 9 a control circuit, and 10 a data processor. The number of the photons I of the fluorescence emitted from the 0.5 mm-long area irradiated by the laser beam can be obtained from the following formula:

$$I \sim I_0 \cdot \phi \cdot [1 - e^{-\epsilon lM}] \sim I_0 \phi \epsilon lM \quad (4)$$

where $I_0$ denotes the number of incident photons, $\phi$ denotes a quantum yield of the fluorophore, $\epsilon$ denotes a mole absorption coefficient, l denotes a optical path length and M denotes a mole concentration of the fluorophore. The number of the photons emitted from the 2.5 mw laser per second (namely, $I_0$) is approximately $10^{16}$. When Texas Red of approximately 0.4 in $\phi$ is irradiated with the light having the wavelength of 594 nm, the absorption coefficient of Texas Red $\epsilon$ is approx. $8 \times 10^4$ cm$^{-1}$(M)$^{-1}$, l is approx. 0.05 cm, and the concentration M of Texas Red showing the same level of fluorescence as that of the gel is approx. $2 \times 10^{-11}$ moles/l. The number of photons I from Texas Red which emits the same amount of the fluorescence as that of background fluorescence from the gel is estimated to be approximately $3 \times 10^8$ per second.

When a 10 cm area is scanned by the laser beam, the duty cycle is 0.5/100. Therefore, the average number of photons emitted from the 0.5 mm-long area is $1.5 \times 10^6$ per second. Even when the lens having a greater F-value is used to receive light, the photodetecting efficiency is 1 to 2 percent when consideration is given to the filter transmittance (approximately 50%). When consideration is given to the quantum yield (approximately 5%) on the photodetecting surface, the number of photons to be received is 1000 per second or less. Thus, the scanning method fails to provide high-precision measurement.

In the lateral incident method proposed in the present invention, however, the duty cycle is 1.0, but since the reduced image is formed on the detector, the photodetecting efficiency is as small as approx. 0.05%. The number of protons emitted from the 0.5 mm-long area which enter the detector is approx. $7.5 \times 10^3$ per second when the quantum efficiency on the photodetecting surface and losses due to various factors are taken into consideration. The detection sensitivity is determined by the fluctuation of the background fluorescence to be measured.

In this case, the statistical fluctuation is approximately ±1.2 percent. Generally, the relative value of the fluctuation is reduced with the increase of the photodetecting quantity, and even a slight signal can be measured. If the photodetecting quantity is increased by N times, the relative fluctuation is reduced to $$\pm \frac{1}{\sqrt{N}}.$$

For example, when the photodetecting quantity is increased by four times, the relative fluctuation is reduced by one half. To ensure highly sensitive detection, the above-said fluctuation of approximately ±1.2% must be further reduced, and the photodetecting quantity must be increased.

To realize this, the present invention uses, a cylindrical convex lens (focal distance f=25 mm, f-number F=1.0) which is installed at a position approximately 25 mm away from the irradiation section, and a cylindrical concave lens (f=−200 mm) which is placed immediately before the lens for image formation so that the image in the vertical direction will be formed in an enlarged size; hence the photodetecting solid angle has been increased four to five times. This has increased the photodetecting quantity by four to five times, and has reduced fluctuation by half down to approximately ±0.6% of the fluorescence emitted from the gel, thereby ensuring a highly sensitive detection capability.

Namely, this detection system permits detection of Texas Red of $2 \times 10^{-13}$ moles/l at a S/N ratio of approximately 1.

When the argon laser is used as an excitation light source, and Texas Red is used as a labeling fluorophore, the excitation efficiency is reduced by one digit compared with that of the present embodiment, and the sensitivity is also reduced undesirably by one digit. When the argon laser is used as an excitation light source, and FITC is used as a labeling fluorophore, the background fluorescence is increased by one digit compared with that of the present embodiment, and the labeling fluorophore is subjected to photodestruction during the measurement so that the effective FITC concentration is reduced. As a result, the sensitivity is also reduced undesirably by two digits compared with that of the present embodiment.

Figure 2:
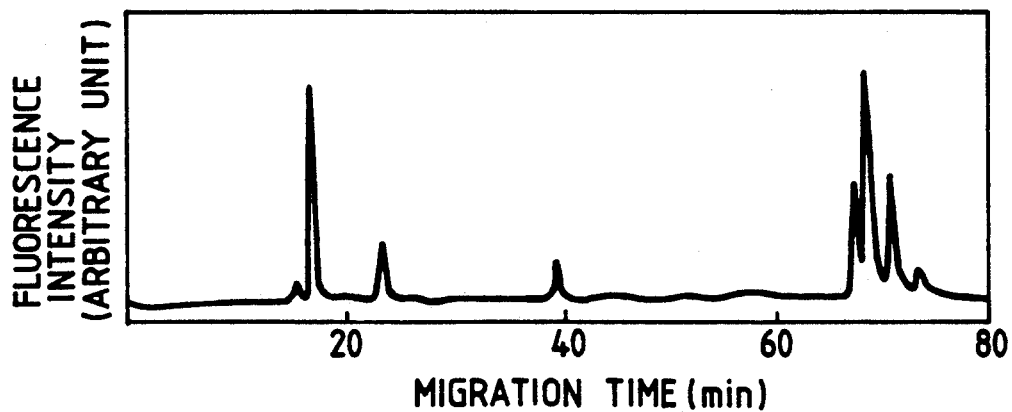
FIG. 2 is a graph representing the spectrum in the electrophoresis separation of the DNA fragment which is obtained by letting the λ phage be digested by the restriction enzyme and by inserting the fluorescence label into the cut portion.

FIG. 2 represents an electrophoresis separation pattern of the fragment which is digested by the enzyme wherein the terminal of the λ phage is labeled by Texas Red and the He-Ne laser of 594 nm wavelength is employed. The cubic volume of the DNA band is estimated at 1 μl, and it is possible to read the signal from the sample which is injected $2 \times 10^{-19}$ moles.

By contrast, the quantity of the sample for which the signal can be read is $1 \times 10^{-17}$ moles per band in the conventional case of using FITC and the argon laser, and is $2 \times 10^{-18}$ moles per band in the conventional case of using Texas Red and the argon laser.

The following Table shows the comparison between an example of the He-Ne laser used in the present invention and an example of the argon laser used in the conventional case. This reveals that the He-Ne laser is smaller in size, lighter in weight and usually less costly than the argon laser.

|  | He-Ne laser | | Argon laser | |
| --- | --- | --- | --- | --- |
|  | Size (cm) | Weight (kg) | Size (cm) | Weight (kg) |
| Power supply | 8 × 15 × 15 | 2 | 15 × 40 × 30 | 20 |
| Resonator | 7 (dia.) × 4 | 2 | 15 × 15 × 35 | 10 |

Thus, the DNA detector of the present invention features not only a higher sensitivity but also a smaller size than the conventional device.

As described above, according to the present invention, Texas Red or rhodamine derivatives having an emission band in the long wave area of less background fluorescence from the gel can be effectively excited by the yellow He-Ne laser with the wavelength of 594 nm, so that this characteristic ensures a higher sensitivity and a smaller configuration.

What is claimed is:

1. A fluorescence detection type electrophoresis DNA detector comprising:
   an electrophoresis separation gel plate including a gel for producing a gel migration of a DNA fragment labeled with a fluorophore introduced into the gel plate;
   a He-Ne laser emitting a laser beam having a wavelength of 594 nm for irradiating the gel plate to excite the fluorophore, thereby causing the fluorophore to emit fluorescence;
   a filter for receiving light from the gel plate including the fluorescence emitted by the fluorophore and passing substantially only the fluorescence emitted by the fluorophore; and
   a photodetector for detecting the fluorescence emitted by the fluorophore passed by the filter.

2. A DNA detector according to claim 1, wherein the fluororphore is Texas Red (sulforhodamine 101).

3. A DNA detector according to claim 1, wherein the filter has a maximum transmission wavelength ranging from 600 to 640 nm.

4. A DNA detector according to claim 1, wherein the filter has a maximum transmission wavelength ranging from 610 to 630 nm.

5. A DNA detector according to claim 1, wherein the He-Ne laser is disposed so as to irradiate a linear portion of the el plate from a side of the gel plate.

6. A DNA detector according to claim 1, further comprising a cylindrical lens disposed between the gel plate and the filter for collecting the light from the gel plate and directing the collected light to the filter.

7. A DNA detecting method comprising the steps of:
   labeling a DNA fragment with a fluorophore selected from Texas Red (sulforhodamine 101) and rhodamine derivatives;
   introducing the DNA fragment labeled with the fluorophore into an electrophoresis separation gel plate including a gel for producing gel migration of the DNA fragment labeled with the fluorophore;
   irradiating the gel plate with a He-Ne laser beam having a wavelength of 594 nm to excite the fluorophore, thereby causing the fluorophore to emit fluorescence; and
   detecting the fluorescence emitted by the fluorophore.

8. A DNA detecting method according to claim 7, wherein the step of irradiating the gel plate includes irradiating a linear portion of the gel plate, and wherein the step of detecting the fluorescence includes the steps of collecting the fluorescence with a cylindrical lens and detecting the fluorescence collected by the cylindrical lens with a photodetector.

* * * * *